United States Patent [19]

Takeuchi et al.

[11] Patent Number: 5,254,464
[45] Date of Patent: Oct. 19, 1993

[54] PROCESS FOR PRODUCING D-ALANINE

[75] Inventors: Masae Takeuchi; Tetsu Yonehara, both of Aichi, Japan

[73] Assignee: Toray Industries, Inc., Japan

[21] Appl. No.: 742,147

[22] Filed: Aug. 1, 1991

Related U.S. Application Data

[63] Continuation of Ser. No. 250,322, Sep. 28, 1988, abandoned.

[30] Foreign Application Priority Data

Oct. 7, 1987 [JP] Japan .................. 62-253127

[51] Int. Cl.$^5$ .............. C12P 13/06; C12N 15/00; C12N 1/20
[52] U.S. Cl. ................. 435/116; 435/172.1; 435/252.8; 435/252.1; 435/840; 435/849
[58] Field of Search .......... 435/252.8, 252.1, 116, 435/840, 849, 172.1

[56] References Cited

U.S. PATENT DOCUMENTS 3,117,915  1/1964  Shiio ............................. 435/843
3,871,959  3/1975  Chibata ......................... 435/116

FOREIGN PATENT DOCUMENTS 42-20683  10/1967  Japan .

OTHER PUBLICATIONS

Adelberg et al, Biochemical and Biophysical Research Communications, vol. 18, No. 5-6, 1965.
Chemical Abstracts, vol. 67 No. 15, Oct. 9, 1967, p. 6700, abstract No. 71293s.
Patent Abstracts of Japan, vol. 8, No. 232(C-248)(1669), Oct. 25, 1984.
Chemical Abstracts, vol. 87, No. 7 Aug. 15, 1977, p. 200, Abstract No. 49947z.
Biotechnology of Amino Acid Production, Progress in Industrial Microbiology, vol. 24, 1986, pp. 3-13.
J. Gen. Appl. Microbiol., vol. 17, No. 2, 1971, pp. 169-172.
David, H. L. Appl. Microbiol. vol. 21, 1971, pp. 888-892.
Robbins et al., J. Bacteriol. vol. 116, 1973, pp. 12-18.
M. Goodfellow et al ed., The Biology of the Actinomycetes, 1984 Academic Press, London pp. 30-31, 44-46 and 77-79.
Brock et al., Biology of Microorganisms 1984 pp. 304-310.
Clark et al, "D-Cycloserine-Induced Alterations in the Transport of D-Alanine and Glycine in Bacillus subtilis 168" Antimicrob. Agents and Chemo. May 1977, pp. 877-880.
Clark et al, "Inducible Resistance to D-cycloserine in Bacillus subtilis 168", Antimicrob. Agents and Chemo., May 1977, pp. 871-876.

Primary Examiner—Irene Marx
Attorney, Agent, or Firm—Austin R. Miller

[57] ABSTRACT

It is possible to produce and accumulate D-alanine selectively and to improve the amount of production and accumulation of D-alanine by cultivating a microorganism having both an ability to produce D-alanine and a resistance to D-cycloserine and belonging to the genus Brevibacterium.

4 Claims, 2 Drawing Sheets

PROCESS FOR PRODUCING D-ALANINE

This application is a continuation of application Ser. No. 07/250,322, filed Sep. 28, 1988 now abandoned.

BACKGROUND OF THE INVENTION

(1) Field of the Invention

The present invention relates to an industrially favorable process for producing D-alanine.

D-alanine is an unnatural amino acid and it is a useful compound for a reagent as it is or for a raw material for synthesizing peptides and so on. Accordingly, the demand has been recently increasing.

(2) Description of the Prior Art

A number of processes for producing DL-alanine by means of a fermentation process using a microorganism belonging to the genus Brevibacterium have been hitherto known. An improved process for producing DL-alanine by using a microorganism belonging to the genus Brevibacterium and having sensitivity against threonine and methionine, also has been known (*J. Gen. Appl. Microbiol.* 1971, 17(2), 169-72).

However, it is inevitable to use a certain optical resolution operation for obtaining only D-alanine, because L-alanine is also produced by these process.

Namely, it has been never achieved yet to produce D-alanine by fermentation with low cost, simply and industrially favorably.

SUMMARY OF THE INVENTION

One of the purposes of the present invention is to offer a process for producing D-alanine by means of an optically selective fermentation method.

The second purpose of the present invention is to offer a process for increasing the accumulative concentration of D-alanine by fermentation using one microorganism.

The third purpose of the present invention is to offer a process for producing D-alanine without using an optical resolution operation.

The fourth purpose of the present invention is to offer a simple process for producing D-alanine at low cost.

The final purpose of the present invention is to offer an industrially favorable process for producing D-alanine.

Other and further objects, features and abvantages of the present invention will appear more fully in the following description.

These purposes can be achieved by a process for producing D-alanine characterized by cultivating a microorganism, which belongs to the genus Brevibacterium and has an ability to produce D-alanine and a resistance to D-cycloserine, producing and accumulating thereby D-alanine in a culture medium, and obtaining D-alanine from the culture broth.

DESCRIPTION OF THE PREFFERED EMBODIMENTS

Figure 1:
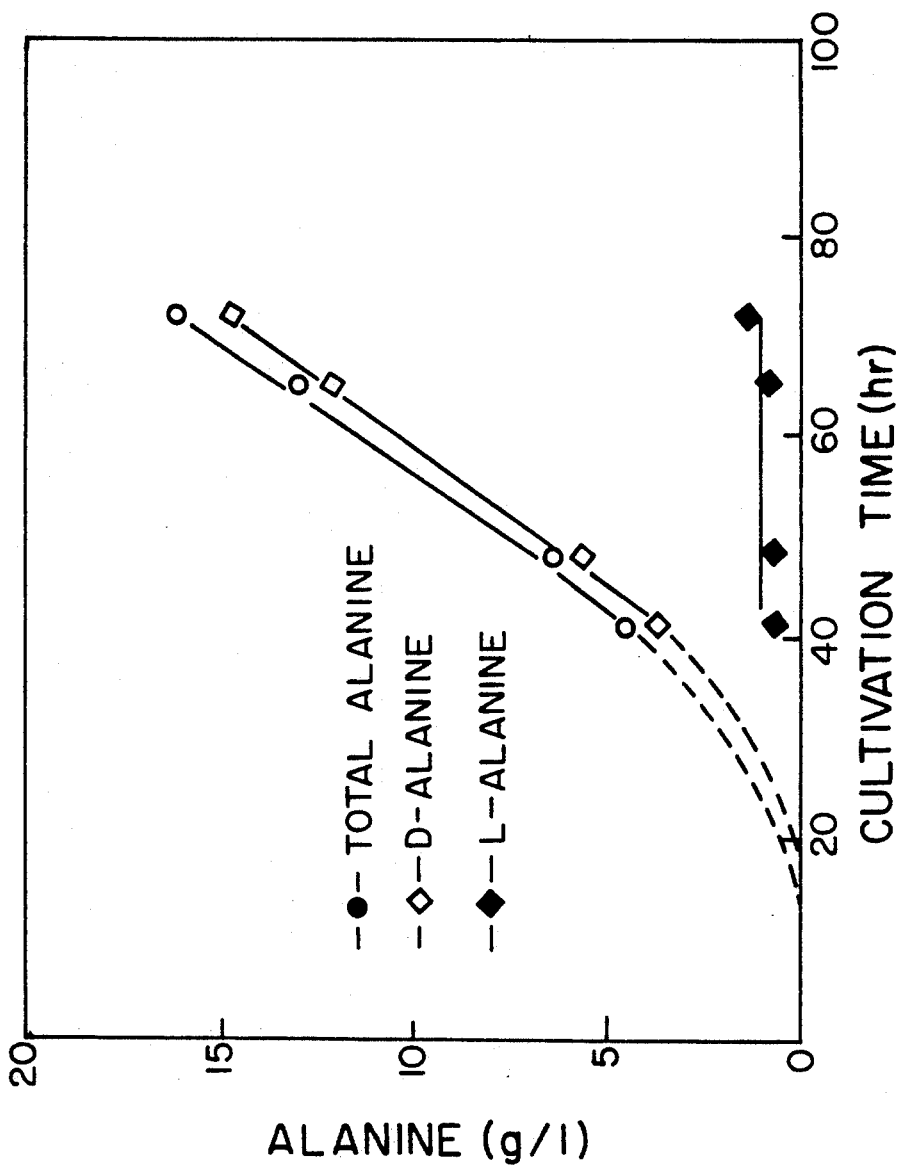
FIG. 1 shows the quantities of D- and L-alanine, respectively, accumulated in the culture medium with the passage of cultivation time.

The microorganisms used in the present invention are those microorganisms that have an ability to produce D-alanine and a resistance to D-cycloserine and belong to the genus Brevibacterium. Whenever any microorganism belonging to the genus Brevibacterium has these characteristics, it can be included in the range of the present invention even if it has other auxotrophy and drug resistance.

Microorganisms which belong to the genus Brevibacterium and have resistance to D-cycloserine can produce and accumulate D-alanine selectively with high accumulation quantity.

As the representative samples of the microorganisms used in the present invention, for example, *Brevibacterium lactofermentum* DCSR-26, *Brevibacterium lactofermentum* DCSR17-2 and *Brevibacterium flavum* DCSR 2-2 can be cited. *Brevibacterium lactofermentum* DCSR-26 is derived from *Brevibacterium lactofermentum* ATCC 13869 (requiring biotin for growth) and it is a variant having resistance to D-cycloserine. *Brevibacterium lactofermentum* DCSR17-2 is derived from *Brevibacterium lactofermentum* DCSR-26 and it is a variant having a further higher resistance to D-cycloserine. *Brevibacterium flavum* DCSR 2-2 is derived from *Brevibacterium flavum* ATCC 13826 and it is a variant having a resistance to D-cycloserine.

*Brevibacterium lactofermentum* DCSR-26 was deposited with the Fermentation Research Institute, Agency of Industrial Science and Technology in Japan (abbreviated as FRI thereinafter) on Sep. 24, 1987 and a registration No. FERM BP-2023 was conferred on it. *Brevibacterium lactofermentum* DCSR 17-2 was deposited with the FRI in Japan on Mar. 9, 1988 and a registration No. FERM BP-2024 was conferred on it. *Brevibacterium flavum* DCSR 2-2 was deposited with the FRI in Japan on Sep. 12, 1988 and a registration No. FERM BP-2047 was conferred on it.

FERM BP number is the registration number of the deposition to FRI based the Budapest Treaty. All restrictions upon availability to the public strains FERM BP-2023, 2024 and 2047 will be irrevocably removed upon granting of the patent and the deposit will be maintained in a public depository for a period of 30 years or 5 years after the last request or for the effective life of the patent, whichever is longer.

FRI is located in 1-1, Higashi 1-Chome, Tsukuba, Ibaraki ken, Japan.

Derivation of the variant can be relatively easily carried out by means of an ordinary mutative treatment. Namely, to obtain variants having resistance to D-cycloserine, parent strains are either irradiated by ultraviolet or treated with mutagenic agents (for example, N-methyl-N'-nitro-N nitrosoguanidine, ethyl methanesulfonate and so on) and strains which are capable of growing distinguishably in comparison with the parent strain can be selected from the culture plates contained D-cycloserine in such a concentration that the parent strain can not grow sufficiently.

D-cycloserine resistant strain in the present invention means the strain gaining stronger resistance than that the parent strain has. The relative growth degree of the D-cycloserine resistant strain is preferably 50% or more when the cultivation is carried out in a culture medium containing D-cycloserine with such a concentration that the relative growth degree of the parent strain becomes 40% or less. Here, the relative growth degree is shown by the percentage of the optical density measured at 660 nm of the culture broth containing no D-cycloserine.

As the culture medium used in the present invention, various nutrient resources being widely used in cultivation of microorganisms can be used. For example, as the carbon source, sugars such as glucose, molasses, hydrolysate of starch and so on, organic acids such as acetic acid, benzoic acid and so on, alcohols such as ethanol and so on can be used and as the nitrogen source, ammonium sulfate, ammonium nitrate, ammonium chloride, ammonium phosphate, urea, ammonia and so on can be used. Depending upon the kind of inorganic ammonium salts, inorganic salts such as phosphate, calcium carbonate and so on are required to use with them. Moreover, to improve the growth of microorganisms and to accumulate large amount of D-alanine, it is preferable to add, for example, organic nitrogen sources, vitamins, a small amount of metal ions and so on in the above described culture medium. Consequently, the purpose can be sufficiently achieved by adding usually cheap natural products such as soybean hydrolysate and corn steep liquor.

In the present invention, it is preferable to add D,L-alanine containing L-alanine with any ratio in the culture medium. As the additive D,L-alanine containing L-alanine with any ratio, not only a racemic modification of D,L-alanine but also pure L-alanine can be used. The time of the addition is not specifically restricted during the cultivation, but the early or intermediate phase of the cultivation is the most effective. By adding D,L-alanine, the ability of D-alanine accumulation by the microorganism used in the present invention can be improved and L-alanine is converted into D-alanine by the action of the microorganism. As the result, the amount of production and accumulation of D-alanine is surprisingly improved. The amount of D,L-alanine to be added is not specifically restricted. The larger the amount added, the higher the amount of accumulation of D-alanine. Usually, it is 100 g/l or less.

In the present invention, the above described cultivation of the microorganism is preferably carried out in an aerobic condition such as shaking or stirring with aeration. The cultivation temperature is usually in the range of 20°-40° C. and especially around 30° C. is preferable. The pH of the medium is usually at 5-9 and it is preferable to keep it at about neutral for obtaining high yield. Thus, after cultivation for several days, a remarkable amount of D-alanine is produced and accumulated in the culture broth. After the cultivation is finished, D-alanine produced can be easily obtained by well known isolation and purification procedures such as ion exchange, adsorption and precipitation procedures without using an optical resolution method.

The present invention will be more clearly understood with reference to the following Experiments and Examples.

EXPERIMENT 1

A. (Separation of D-cycloserine resistant strains)

Cells of *Brevibacterium lactofermentum* ATCC 13869 (requiring biotin for the growth) were treated with N-methyl-N'-nitro-N-nitrosoguanidine (300 μg/ml, at 30° C. for 10 minutes) by means of a usual procedure and then spread on the complete synthetic agar plate containing 50 mg/l of D-cycloserine (the complete synthetic agar plate: 2% of gulcose, 2% of agar, 1% of ammonium sulfate, 0.1% of potassium hydrogen-phosphate, 0.04% of 7 hydrate of magnesium sulfate, 0.05% of sodium chloride, 0.25% of urea, 10 mg/l of 7 hydrate of ferrous sulfate, 10 mg/l of 4 hydrate of manganese (II) sulfate and 50 μg/l of biotin). Then, the incubation was carried out at 30° C. for 5-7 days and large colonies appeared were separated by means of colony picking to select a D-cycloserine resistant strain (*Brevibacterium lactofermentum* DCSR-26).

Another D-cycloserine resistant strain (*Brevibacterium flavum* DCSR 2-2) was obtained in the same way as the above described procedures such as mutation, cultivation and separation of the strain except that *Brevibacterium lactofermentum* ATCC 13869 was replaced with *Brevibacterium flavum* ATCC 13826.

Moreover, cells of *Brevibacterium lactofermentum* DCSR-26 were treated with N-methyl-N'-nitro-N-nitrosoguanidine (300 μg/ml, at 30° C. for 10 minutes) by means of a usual procedure and then spread on the complete synthetic agar plate containing 100 mg/l of D-cycloserine (the complete synthetic medium: 2% of glucose, 2% of agar, 1% of ammonium sulfate, 0.1% of potassium hydrogen-phosphate, 0.04% of 7 hydrate of magnesium sulfate, 0.05% of sodium chloride, 0.25% of urea, 10 mg/l of 7 hydrate of ferrous sulfate, 10 mg/l of 4 hydrate of manganese (II) sulfate and 50 μg/l of biotin). Then, the cultivation was carried out at 30° C. for 5-7 days and large colonies appeared were separated by means of colony picking to select a D-cycloserine highly resistant strain (*Brevibacterium lactofermentum* DCSR 17-2).

B. (The degree of resistance of D-cycloserine resistant strains)

Each strain shown in Table 1 was cultivated with shaking by using a bouillon liquid medium at 30° C. for 16 hours and the cells grown were harvested and washed well with sterilized physiological saline. These cell suspensions were inoculated in 5 ml of minimal media contained D-cycloserine in concentrations of 0, 10 and 50 mg/l, respectively, (the minimal medium containing 2% of glucose, 1% of ammonium sulfate, 0.1% of potassium hydrogen-phosphate, 0.04% of 7 hydrate of magnesium sulfate, 0.05% of sodium chloride, 0.25% of urea, 10 mg/l of 7 hydrate of ferrous sulfate, 10 mg/l of 4 hydrate of manganese (II) sulfate and 50 μg/l of biotin) and cultivations were continued for 64 hours at 30° C. to investigate the degree of growth of each strain. The results are shown in Table 1.

It is clear from the data shown in Table 1 that D-cycloserine resistant strains used in the present invention (*Brevibacterium lactofermentum* DCSR-26, *Brevibacterium lactofermentum* 17-2 and *Brevibacterium flavum* DCSR 2-2) grew without obstruction by D-cycloserine and are resistant to D-cycloserine in comparison with the respective parent strains, *Brevibacterium lactofermentum* ATCC 13869 and *Brevibacterium flavum* ATCC 13826.

TABLE 1

| | Relative growth degree (%) | | |
| | Concentration of D-cycloserine added (mg/l) | | |
| Strain | 0 | 10 | 50 |
---
| Parent strain | 100 | 36.7 | 0 |
| *Brevibacterium* | (60.0) | (22.0) | (0) |
| *lactofermentum* | | | |
| ATCC 13869 | | | |

TABLE 1-continued

| | Relative growth degree (%) | | |
|---|---|---|---|
| | Concentration of D-cycloserine added (mg/l) | | |
| Strain | 0 | 10 | 50 |
| Strain of the present invention *Brevibacterium lactofermentum* DSCR-26 | 100 (87.0) | 78.4 (68.2) | 61.8 (53.8) |
| Strain of the present invention *Brevibacterium lactofermentum* DCSR 17-2 | 100 (92.9) | — | 109 (101.7) |
| Parent strain *Brevibacterium flavum* ATCC 13826 | 100 (125.2) | 87 (109.0) | 82 (103.0) |
| Strain of the present invention *Brevibacterium flavum* DCSR 2-2 | 100 (103.1) | 103 (106.6) | 107 (110.8) |

Notice: Optical densities at 660 nm of culture broths were shown in ( ). The relative growth degree as calculated by using the optical density of the culture broth where no D-cycloserine was added as 100%.

EXAMPLE 1

Each 40 ml of fermentation medium (pH 7.25) containing 10% of glucose, 1.8% ammonium sulfate, 0.05% of di-potassium hydrogenphosphate, 0.025% of 7 hydrate of magnesium sulfate, 0.001% of zinc chloride, 2% of soybean hydrolysate (Ajinomoto, Tokyo, Japan), 3% of calcium carbonate and 30 μg/l of biotin was poured into a 1-l Erlenmeyer flask and sterilized in an autoclave at 120° C. for 10 minutes to obtain fermentation medium. *Bravibacterium lactofermentum* DCSR-26 and its parent strain, *Brevibacterium lactofermentum* ATCC 13869 were inoculated in a bouillon liquid medium respectively and cultivated with shaking at 30° C. for 5 days. 1% of the above described each culture medium was put into the above described fermentation medium respectively. After shaking at 30° C. for 5 days, D-alanine was produced in each culture medium as shown in Table 2.

TABLE 2

| | Strain | Amount of D-alanine accumulated | Purity* |
|---|---|---|---|
| Comparative example | *Brevibacterium lactofermentum* ATCC 13869 | 9.2 g/l | 76% |
| Example of the present invention | *Brevibacterium lactofermentum* DCSR-26 | 13.2 g/l | 100% |

*Purity = $\frac{\text{D-alanine (g/l)}}{\text{Total alanine (g/l)}} \times 100\%$ The total amount of alanine in the fermentation medium was analysed by means of an automatic amino acid analyzer. Analysis of D-alanine was carried out both by means of an enzymatic method using D-amino acid oxidase and by means of high performance liquid chromotography (HPLC) using a column for optical resolution (Sumitomo Chemical Industries, Co., Ltd OA-1000).

The Cells were removed by means of centrifugal separation from 1 l of the fermentation broth of *Brevibacterium lactofermentum* DCSR-26 to obtain a supernatant liquid which was then decolorized with active carbon powder. The decolorized liquid thus obtained was passed through a column where a strong cation exchange resin "DIAION SK-1B" (H+ type) was packed to adsorb D-alanine, which was eluted with 2N aqueous ammonia after washing with water. The eluted fractions of D-alanine were concentrated and ethanol was added to the concentrated liquid to obtain precipitated crystals. 9.5 g of D-alanine crystals were obtained by recrystalizing with ethanol.

Specific rotation $[\alpha]_D^{25} = -14.2°$ (C=6, 1N—HCl).

EXAMPLE 2

1 l of the fermentation medium described as in Example 1 without calcium carbonate were put into a jarfermenter and sterilized. *Brevibacterium lactofermentum* DCSR 17-2 was cultivated in the bouillon liquid medium at 30° C. for 16 hours. Then, 40 ml of this culture medium was inoculated in the above described 1-l fermentation medium and fermentation was continued aerobically (1 v.v.m., impeller speed: 600 r.p.m.) for 3 days at 30° C. to produce 14.8 g/l of D-alanine in the broth. The relation between the cultivation time and the accumulated amount of alanine for 3 days is shown in FIG. 1.

D-alanine was separated and obtained from 1 l of the culture broth by the same procedure as described in Example 1 and 11.8 g of D-alanine crystals were thereby obtained.

Specific rotation $[\alpha]_D^{25} = -14.2°$ (C=6, 1N—HCl).

EXAMPLE 3

Figure 2:
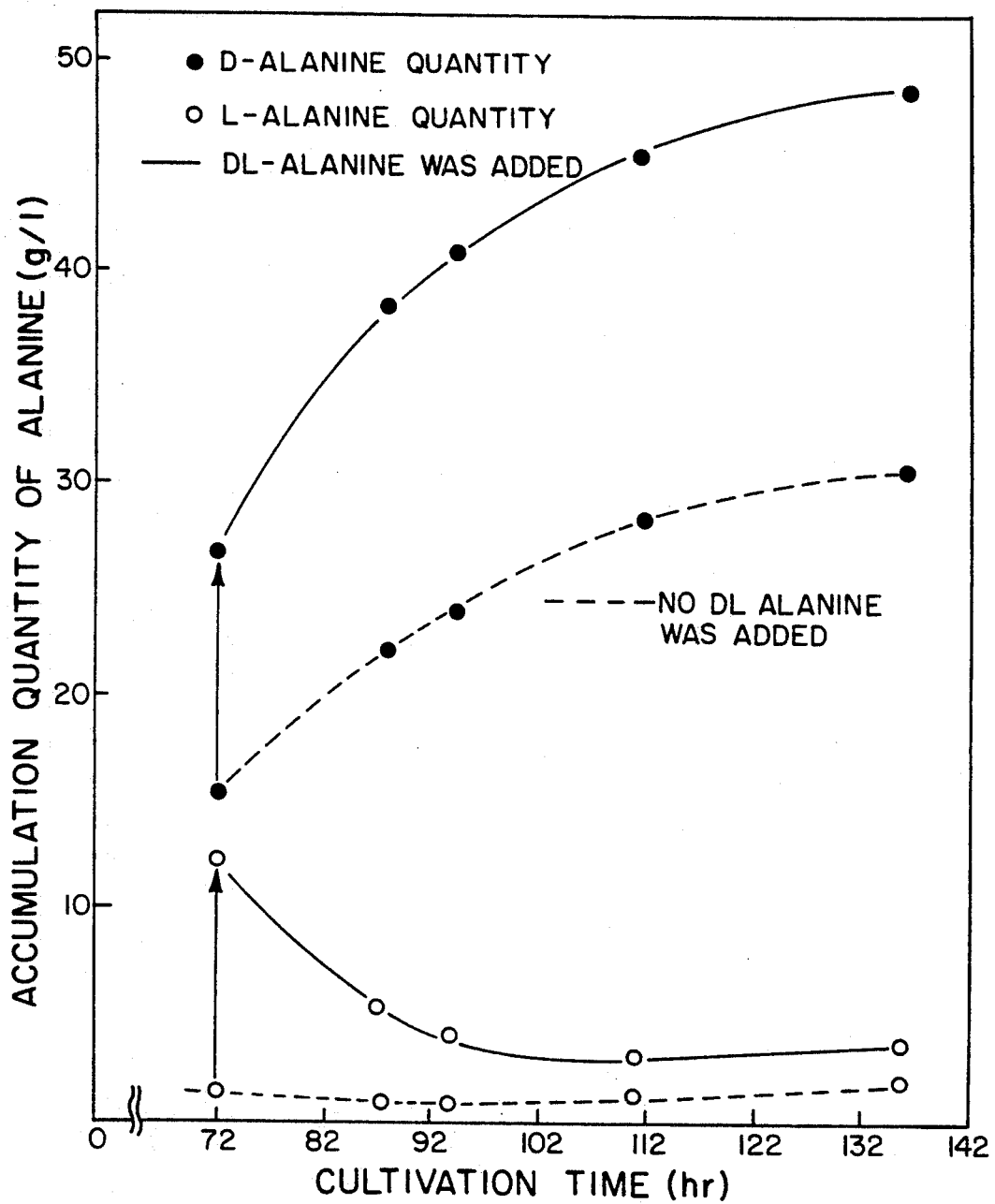
FIG. 2 shows the quantities of D- and L-alanine, respectively, accumulated in the culture medium with the elapse of cultivation time.

40 ml of fermentation medium (pH 7.25) containing 10% of glucose, 3% of ammonium sulfate, 0.05% of potassium hydrogen-phosphate, 0.05% of dipotassium hydrogen-phosphate, 0.025% of 7 hydrate of magnesium sulfate, 2% of soybean hydrolysate, 3% of calcium carbonate and 30 μg/l of biotin was poured into a 1-l Erlenmeyer flask and sterilized in an autoclave at 120° C. for 20 minutes to obtain culture medium. *Brevibacterium lactofermentum* DCSR 17-2 was inoculated in the fermentation medium thus obtained and cultivated at 30° C. for 3 days. 20 g/l of racemic D,L-alanine was therein added and the cultivation was furthermore carried out for 64 hours to produce and accumulate 48.8 g/l of D-alanine in the culture broth as shown in FIG. 2.

The supernatant liquid obtained by removing cells from 200 ml of this culture broth by means of centrifugal separation was decolorized with active carbon powder. The decolorized liquid was passed through a column where a strong cation exchange resin "DIAION SK-1B" (H+ type) was packed to absorb D-alanine, which was eluted with 2N aqueous ammonia after washing with water. The eluted fractions of D-alanine were concentrated and ethanol was added to concentrated liquid to obtain precipitated crystals. 7.2 g of D-alanine crystals were obtained by recrystalizing with ethanol.

Optical purity: 99.4%.

Specific rotation: $[\alpha]_D^{25} = -14.2°$ (C=6, 1N—HCl).

Analysis of D-and L-types of alanine was carried out in the same way as described in Example 1.

EXAMPLE 4

Each 40 ml of fermention medium (pH 6.5) containing 10% of glucose, 2% of ammonium sulfate, 0.05% of potassium hydrogen-phosphate, 60 μg/l of biotin, 1% of sodium chloride, 10 mg/l of 7 hydrate of ferrous sulfate, 20 mg/l of 4 hydrate of manganese (II) sulfate, 0.025% of 7 hydrate of magnesium sulfate and 2% of hot water extract of bean cake was poured into a 1 l Erlenmeyer flask and sterilized in an autoclave at 120° C. for 20 minutes to obtain culture medium. *Brevibacterium flavum* ATCC 13826 and *Brevibacterium flavum* DCSR 2-2 were respectively inoculated in the fermentation media thus obtained and shaken at 30° C. for 3 day. D-alanine was thereby produced in each culture broth as shown in Table 3.

TABLE 3

|  | Strain | Amount of D-alanine accumulated | Purity | D/L ratio* |
|---|---|---|---|---|
| Comparative example | *Brevibacterium flavum* ATCC 13826 | 1.7 g/l | 85% | 6.96 |
| Example of the present invention | *Brevibacterium flavum* DCSR 2-2 | 1.9 g/l | 95% | 13.4 |

*D/L ratio = $\dfrac{\text{Amount of D-alanine}}{\text{Amount of L-alanine}}$

As the D/L ratio was larger than 10 in the Example of the present invention, it was possible to separate D-alanine with almost no loss by means of recrystallization.

What we claim is:

1. A process for producing D-alanine comprising cultivating a mutant derived from a parent strain selected from the group consisting of *Brevibacterium lactofermentum* ATCC 13869 and *Brevibacterium flavum* ATCC 13826 which has the ability to produce D-alanine from assimilable carbon and nitrogen sources other than alanine and resistance to 50 mg/l of D-cycloserine, producing and accumulating thereby D-alanine in a culture broth and recovering D-alanine from the culture broth.

2. A process according to claim 1 wherein said mutant is *Brevibacterium lactofermentum* FERM BP-2023 (DCSR 26).

3. A process according to claim 1 wherein said mutant is *Brevibacterium lactofermentum* FERM BP-2024 (DCSR 17-2).

4. A process according to claim 1 wherein said mutant is *Brevibacterium flavum* FERM BP-2047 (DCSR 2-2).

* * * * *